(12) United States Patent
Wang et al.

(10) Patent No.: US 11,324,456 B2
(45) Date of Patent: May 10, 2022

(54) DEEP EAR SENSOR FOR REDUCING NOISE FROM MOVEMENT AND ENVIRONMENT

(71) Applicant: Sonova AG, Stafa (CH)

(72) Inventors: Frank Wang, San Bruno, CA (US); Michael Au, Union City, CA (US); Santi Chrisanti, Santa Clara, CA (US); Xiuming Zhu, San Jose, CA (US); Lu Zhang, Fremont, CA (US); Seyedeh Fatemeh Khatami Firoozabadi, Fremont, CA (US); Grace Gardner, San Leandro, CA (US)

(73) Assignee: SONOVA AG, Stäfa (CH)

( * ) Notice: Subject to any disclaimer, the term of this patent is extended or adjusted under 35 U.S.C. 154(b) by 0 days.

(21) Appl. No.: 16/578,650

(22) Filed: Sep. 23, 2019

(65) Prior Publication Data

US 2021/0085254 A1 Mar. 25, 2021

(51) Int. Cl.
*A61B 5/00* (2006.01)
*H01L 31/0232* (2014.01)
*H04R 1/10* (2006.01)

(52) U.S. Cl.
CPC ...... *A61B 5/7228* (2013.01); *H01L 31/02327* (2013.01); *H04R 1/1016* (2013.01); *H04R 1/1083* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,539,440 A | * | 9/1985 | Sciarra | H04R 25/652 381/329 |
| 2009/0074220 A1 | * | 3/2009 | Shennib | H04R 25/456 381/325 |
| 2011/0019851 A1 | * | 1/2011 | Michel | H04R 25/652 381/326 |
| 2014/0010396 A1 | * | 1/2014 | Karamuk | H04R 25/02 381/328 |
| 2020/0085326 A1 | * | 3/2020 | Fransen | A61B 5/02416 |
| 2020/0196073 A1 | * | 6/2020 | Nielsen | A61B 5/6817 |
| 2021/0298619 A1 | * | 9/2021 | Stephenson | H04R 25/652 |
| 2021/0298670 A1 | * | 9/2021 | Roeck | A61B 5/02416 |

* cited by examiner

*Primary Examiner* — Angelica M McKinney
(74) *Attorney, Agent, or Firm* — Pearne & Gordon LLP (57) ABSTRACT

An in-ear optical sensor device sits deep within the ear canal of a subject such that is in the cartilaginous region and/or the bony region of the ear canal where effects from temporomandibular joint activity or other movement, and external light, are limited. The device has a lateral housing and a medial articulating head joined at an articulation joint so that the medial articulating head may be angled relative to the lateral housing to help the device fit within tortuous ear canals. The device also includes a seal configured to conform to the shape of the ear canal to physically support the device to further limit movement and block environmental light. An audio receiver is also included in the device.

15 Claims, 10 Drawing Sheets

DEEP EAR SENSOR FOR REDUCING NOISE FROM MOVEMENT AND ENVIRONMENT

BACKGROUND

Optical sensors use a light source to emit light into an environment and a photodetector to detect light from the environment in order to obtain information about the environment. For instance, optical sensors of that kind are often employed to project light into tissue (e.g., skin) of a subject and a photodetector to measure reflected or transmitted light characteristics of the projected light. The detected light characteristics, a photoplethysmogram (PPG) signal, can be processed to determine heart rate, blood pressure, and other physiological properties. Although there are many places on the body where data can be gathered (e.g., where blood vessel density and tissue type and thickness are optimal for optical transmission and reflectance), some are more prone to effects of noise caused by movement and by ambient light from the environment. Additional factors that can affect quality of PPG signals include the measurement location, type of light used, movement, light from the environment, skin type, and activity of the subject.

In many cases an accelerometer is thus used along with signal processing algorithms to either truncate bad data or filter out the effects of movement from the data based on readings from the accelerometer. In other instances, form factors utilize contact optical sensors where the light source and detector are in contact with the skin to prevent leakage of emitted light and bleeding of light from the environment into the detector. Such sensors can reduce noise caused by ambient light.

Some optical sensors are designed to take measurements at the ear of a subject. One design among these includes a contact optical sensor that has a photodetector angled approximately 45 degrees from its light source. An ear tip of the device, where the sensor is located, is inserted into the ear and retention loop around the outer ear is used to secure the sensor device. However, due to the placement of the sensor on the ear tip, the device is optimally worn on the right ear as wearing it on the left ear would cause the photodetector to be more exposed to environmental light. Further, the ear tip sizes are standardized and thus do not fit all ear canal geometries. And even with the retention loop, the device can migrate while worn. Such movements are particularly pronounced during repetitive movements such as chewing and swallowing. Still further, the device does not guard against sweat or bodily fluids inside the ear canal that can cover the light source and photodetector.

BRIEF SUMMARY OF THE INVENTION

According to one example of the present disclosure, an optical sensor device comprises: an audio receiver configured to deliver a sound to a subject; a light source; a photodetector; a lateral body that houses the audio receiver; a medial head that houses the photodetector; and a seal surrounding a portion of the lateral body or the medial head, wherein the optical sensor device is configured to be inserted into an ear canal of the subject such that the medial head is closer than the lateral body to the tympanic membrane of the subject.

According to various embodiments of the above example, the audio receiver is communicatively coupled to a sound processor configured to provide an audio signal to the audio receiver, the audio signal representative of the delivered sound; the sound processor is communicatively coupled to a microphone configured to detect sound, wherein the audio signal is representative of the detected sound; an inner surface of the seal is corrugated such that the seal is configured to buckle upon application of radial pressure; the medial head is an articulating head that is pivotably attached to the lateral body about an articulation joint; the medial articulating head is pivotable to at least 20 degrees relative to the lateral body; the light source is a light emitting diode; the optical sensor device comprises two seals, wherein: a first seal of the two seals is located at a lateral end of the lateral body, a second seal of the two seals is located at a medial end of the lateral body, and the light source is located between the lateral end and the medial end of the lateral body; the optical sensor device comprises two seals, wherein: a first seal of the two seals is located at a lateral end of the lateral body, the light source is located at a medial end of the lateral body, and a second seal of the two seals is located between the lateral end and the medial end of the lateral body; the light source is housed in the lateral body and is located medial to the seal; the light source is housed in the lateral body and is located lateral to the seal; the light source is housed in the medial head and the seal is located at the lateral body; when the optical sensor device is inserted into an ear canal of the subject, the optical sensor device is at least partially located in a bony region of the ear canal; and/or the optical sensor device is configured to perform photoplethysmography (PPG) based on light detected by the photodetector.

According to another example, an optical sensor device comprises: an audio receiver communicatively coupled to a sound processor, the audio receiver being configured to deliver sound based on an audio signal provided by the sound processor to a subject; a light source configured to emit light into a wall of an ear canal of the subject; a photodetector configured to detect the emitted light that has been reflected and/or absorbed and reemitted by physiological structures within the wall of the ear canal; a lateral body that houses the audio receiver; a medial articulating head that houses the photodetector; and a corrugated seal configured to buckle upon application of radial pressure, the seal surrounding a portion of the lateral body, wherein: the medial head is pivotably attached to the lateral body about an articulation joint such that the medial head is pivotable to at least 20 degrees relative to the lateral body, and the optical sensor device is configured to be inserted into an ear canal of a subject such that the medial articulating head is closer than the lateral body to the tympanic membrane of the subject and the optical sensor device is at least partially located in a bony region of the ear canal.

DETAILED DESCRIPTION OF THE INVENTION

Considering the above, current optical sensors for the ear suffer from poor signal quality and inaccurate measurements. Accordingly, the present disclosure relates to an in-ear optical sensor device that is capable of reducing the effects of movement and ambient light on optical signals, such as PPG signals, measured inside the ear canal.

Figure 1A:
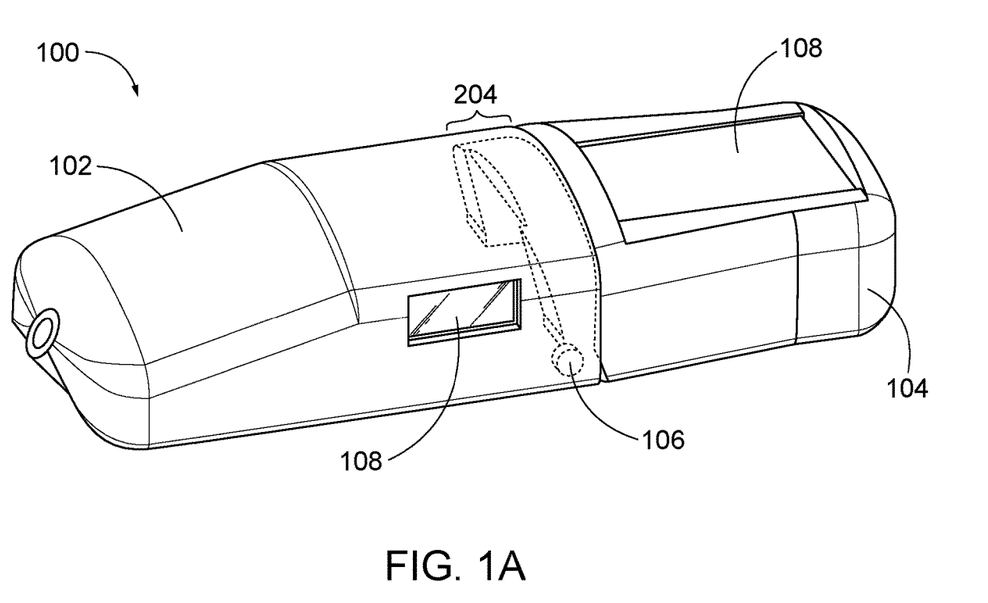
FIGS. 1A and 1B illustrate perspective and side views, respectively, of an example in-ear device according to the present disclosure.
Figure 1B:
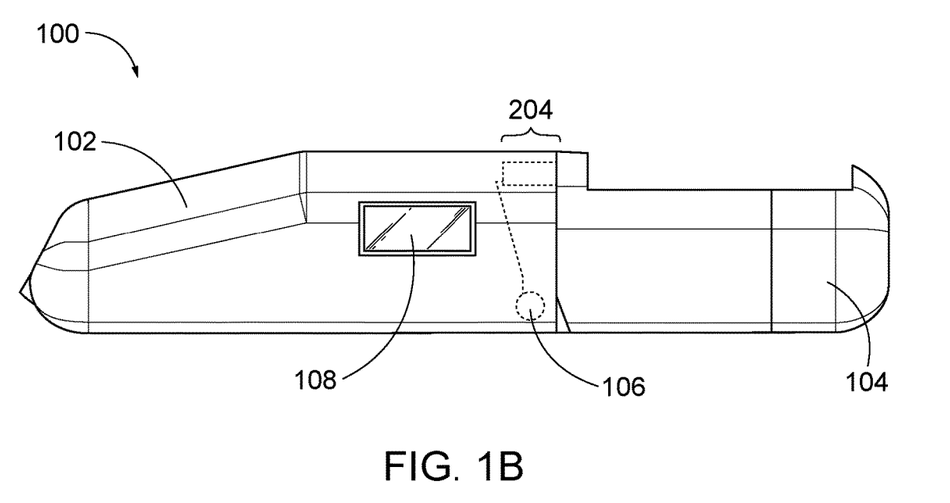

As depicted in FIGS. 1A and 1B, an example in-ear device 100 according to the present disclosure includes a lateral housing 102 and a medial head 104. Medial head 104 is a medial articulating head joined with lateral housing 102 at an articulation joint 106. The lateral housing 102 includes an audio receiver and the medial articulating head 104 includes a photodetector. One or more light sources (e.g., LEDs) can be disposed at any position on the device 100 lateral to the photodetector. In this manner, the in-ear device 100 can be inserted into the ear canal of a subject, leading with the medial articulating head 104 so that the medial articulating head is closest to the tympanic membrane. Light from the LED(s) can then be directed medially toward the medial articulating head 104 where it can be detected by the photodetector. Accordingly, portions of the lateral housing 102 corresponding to the location of the LED(s) and of the articulating head 104 corresponding to the location of the photodetector are preferably transparent, at least for the wavelengths of light transmitted by the LEDs and detected by the photodetector. These transparent portions may be transparent portions of the material forming the lateral housing 102 and/or articulating head 104, or may be windows 108 in the housing (e.g., an aperture filled with a transparent material). "Lateral" and "medial", as used herein, may refer to a relative distance to the tympanic membrane, wherein "medial" denotes a smaller distance from the tympanic membrane than "lateral". "Lateral end" may denote an end opposing the tympanic membrane. "Medial end" may denote an end facing the tympanic membrane.

Preferably the device 100 sits deep within the ear canal, for example, in the cartilaginous region, the bony region, or an overlapping region including both cartilage and bone. Such a location is anatomically less effect by temporomandibular joint (TMJ) activity or other movement, and thus the device 100 is less prone to migration. Further, locations deep within the ear canal are darker, thereby limiting the effects of environmental light that may be detected by the photodetector.

Figure 2A:
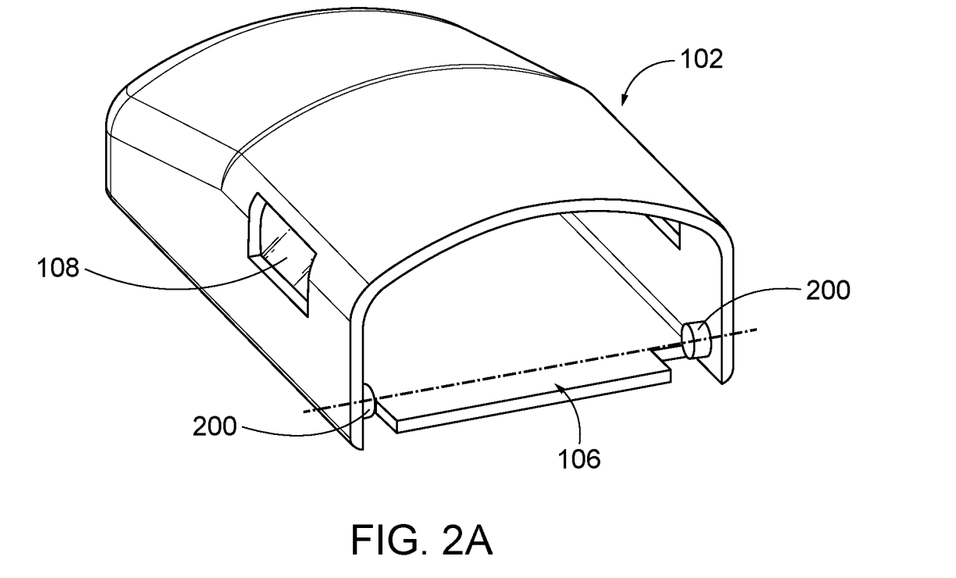
FIGS. 2A and 2B illustrate perspective views, respectively, of an example lateral housing and medial articulating head of an in-ear device according to the present disclosure.
Figure 2B:
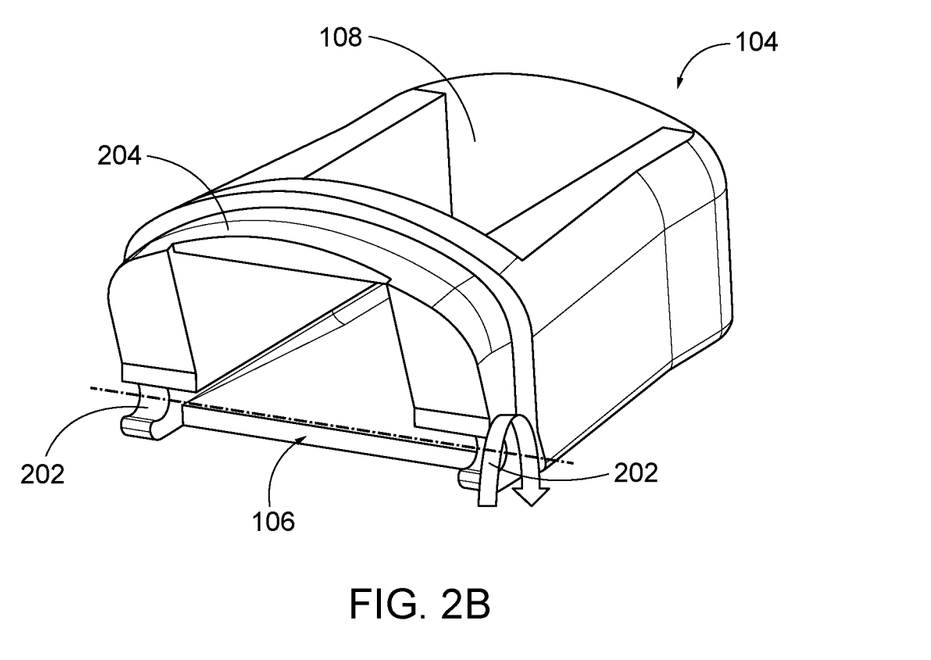

As seen in FIGS. 2A and 2B, the articulation joint 106 is formed by knobs 200 on interior side walls of the lateral housing 102 and corresponding recesses 202 in which the knobs mate on the lateral facing side of the medial articulating head 104. Such a configuration allows the recesses 202 of the articulating head 104 to pivot or rotate about the knobs 200 of the lateral housing 102. When mated, a lateral portion 204 of the articulating head 104 is preferably recessed within the lateral housing 102. This may be achieved by increasing the length of the medial articulating head 104 on a side opposite the recesses of the articulation joint 106. Accordingly, as the medial articulating head 104 is pivoted about the articulation joint 106, the contents of the lateral housing 102 and articulating head 104 remain enclosed. In other embodiments, the various features of the articulation joint 106 may be located on either the lateral housing 102 or the articulating head 104.

Figure 3:
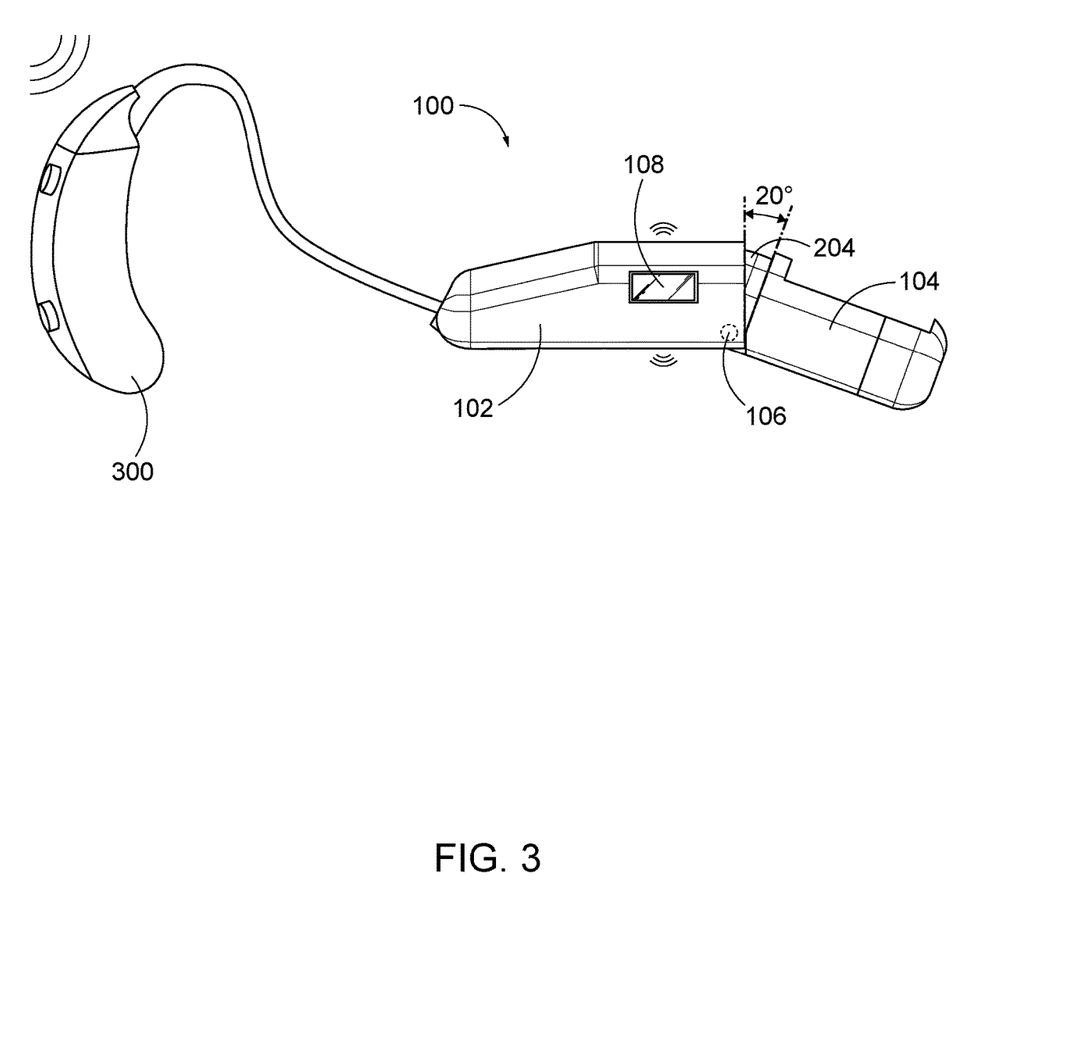
FIG. 3 illustrates articulation of the medial articulating head about the articulation joint of an example in-ear device according to the present disclosure.

The articulating head 104 may be articulated about the articulation joint 106 where a subject's ear canal does not support a wholly linear device 100, for example, where the ear canal is tortuous. Such articulation of the device 100 of 0 degrees is shown in FIG. 3. Preferably, the articulation joint 106 supports articulation of at least 20 degrees. This ability to articulate the articulating head 104 and thus the photodetector 106 therein, can help align the photodetector within a cross-sectional center of the ear canal to improve detection of light from the light source(s).

As noted above, the lateral housing 102 may include an audio receiver. In some embodiments the receiver may be communicatively coupled to an external sound processor 300 that is not within the ear canal. The external sound processor may be implemented, for example, in a behind-the-ear (BTE) hearing device, such as those used in hearing aids and implants. Such external sound processors 300 have a microphone and signal processing circuits and/or processors. The microphone detects external noise, which is then processed by the signal processing components of the sound processor 300. In these embodiments the receiver would be configured to receive an output of the sound processor and supply the processed sound detected by the microphone to the ear canal of the individual wearing the device 100. In other embodiments, the sound may alternatively be processed entirely by the audio receiver, or the audio receiver may provide additional processing to the detected sound. To this end, the audio receiver may comprise a sound processor. In still other embodiments, the audio receiver itself may comprise a microphone and sound processing circuitry and/or processors, thereby detecting the sound itself without an external microphone and external sound processor 300.

The audio receiver may be coupled to the sound processor 300 electrically via wires, wirelessly, induction, or other short range communication protocols. The receiver may comprise further sound processing circuitry and/or processors, and an output device such as a speaker for delivering sound to the subject. The receiver may also be configured to be coupled to the ear canal via bone conduction for delivery of sound to the subject wearing the device 100.

In addition to the above-described components contained in the lateral housing 102 and the medial articulating head 104, the device 100 may also include circuitry and/or processors for performing signal processing of the signals detected by the photodetector. Further, the device 100 may include an accelerometer for detecting movement of the device 100 in the ear canal, so that the effects of the movement can be mitigated during signal processing of the output of the photodetector. These additional components can be distributed in any manner between the lateral housing 102 and the medial articulating head 104 on one or more circuit boards (e.g., printed circuit boards) or substrates (e.g., flexible substrates).

As also noted above, the LEDs (or like light sources) of the device 100 can be located anywhere along the device 100 facing the walls of the ear canal. Preferably the LEDs are housed within the lateral body 102 or medial articulating head 104 so as to be protected from the debris, fluid, and the like within the ear canal. As noted above, portions of the device 100 corresponding to the location of LEDs are preferably transparent to the wavelengths of light emitted by the LEDs, for example, via apertures, windows 108, or material selection of the device. Depending on the embodiment, any number of light sources may be utilized, and the light sources may be configured to output any wavelength of light. For example, there may be at least two LEDs configured to emit green light.

Figure 4A:
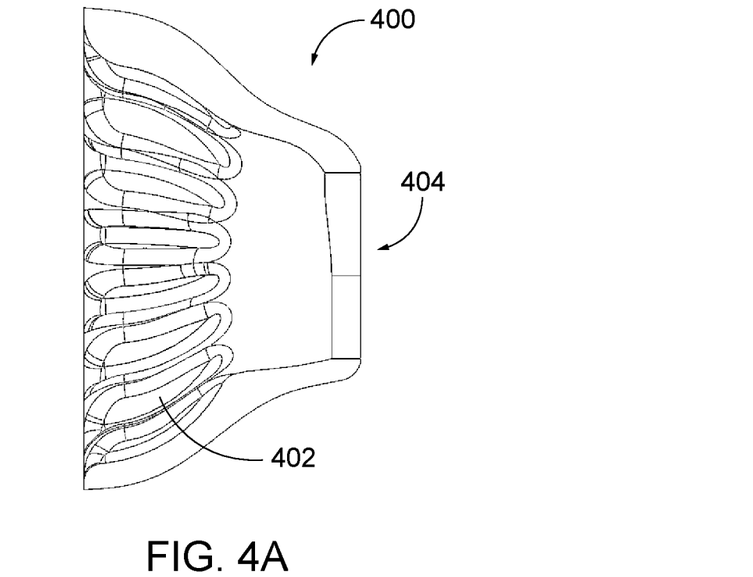
FIGS. 4A and 4B illustrate side cross-sectional and lateral front views, respectively, of an example seal for an in-ear device according to the present disclosure.
Figure 4B:
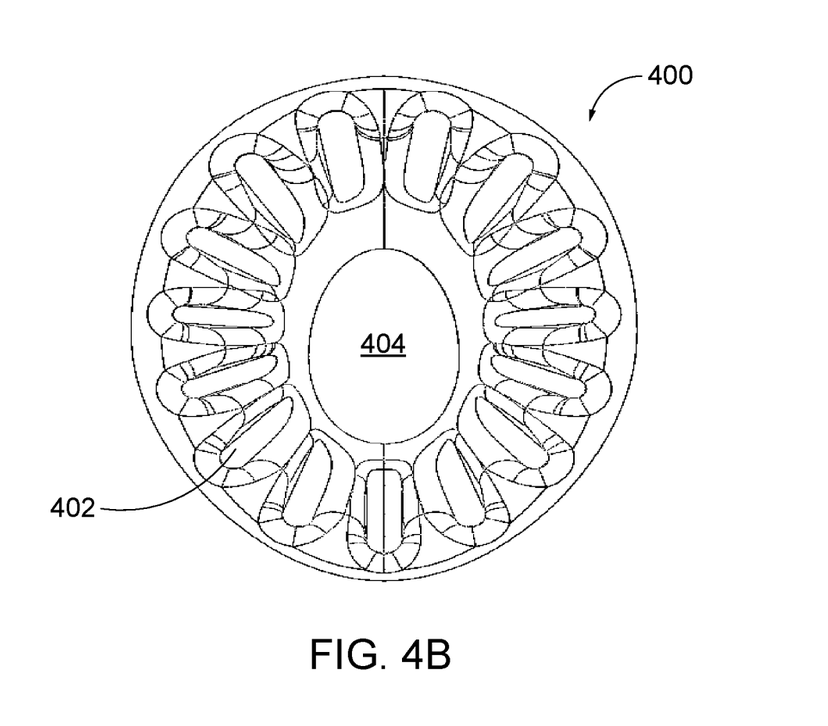

In addition to the internal components, the device 100 preferably also includes at least one seal 400 that surrounds a periphery of the lateral housing 102. The seal 400 is configured to conform to the shape of the ear canal to physically support the device 100, thereby limiting movement and blocking ambient environmental light from passing through the ear canal to the photodetector. In one embodiment the seal 400 may take a generally circular or oval shape in accordance with the general shape of the ear canal, and have a flared circumference to conform to different sized-ear canals. The seal 400 may further be scalloped having a plurality of indentations 402 on an interior surface. In other words, the interior surface of the seal 400 may be corrugated. Accordingly, the seal 400 is configured to buckle at the indentations 402 when radial pressure from the ear canal is applied, thereby reducing wrinkling of the seal 400 that could allow ambient light to pass through to the more medially located photodetector. In short, the seal 400 serves to suspend the device and conform to ear canal shapes and changes to limit movement of the device 100. This further allows the device 100 to be worn in either ear without affecting its performance.

Figure 5A:
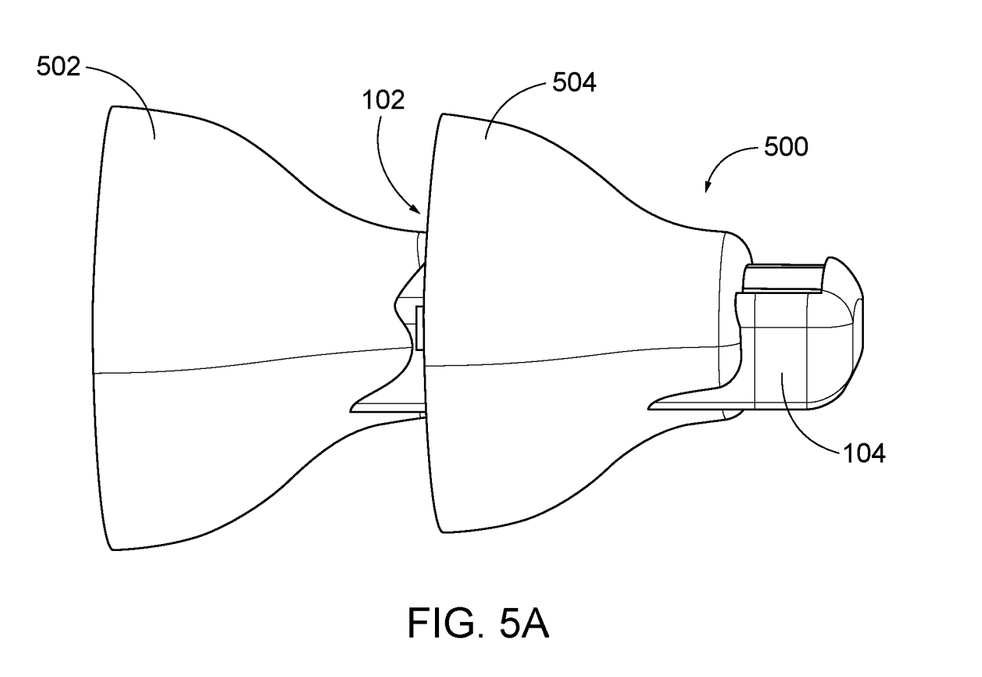
FIGS. 5A and 5B illustrate an example in-ear device having seals according to the present disclosure.
Figure 5B:
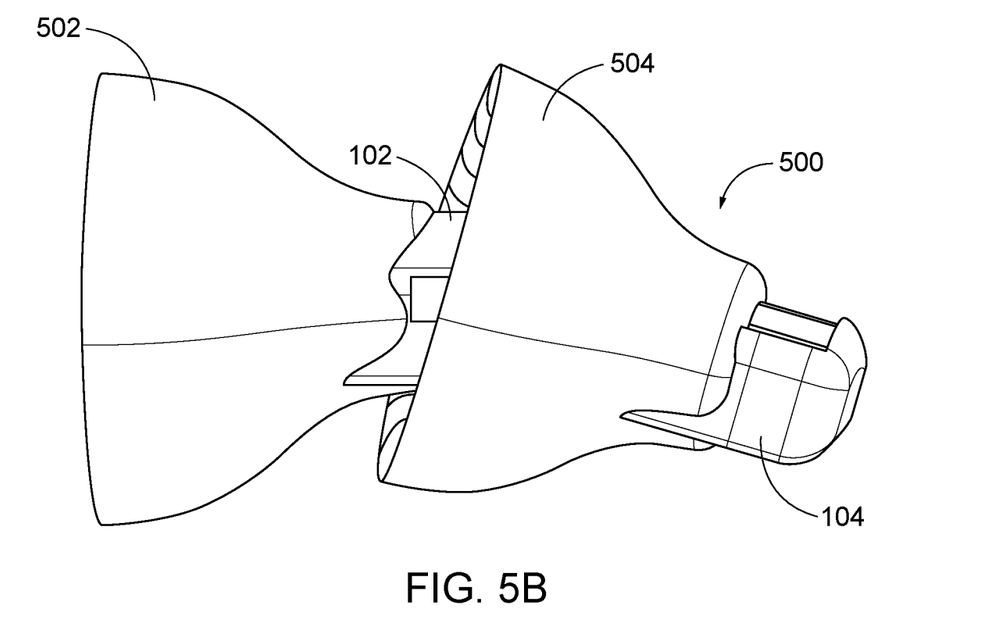
Figure 6:
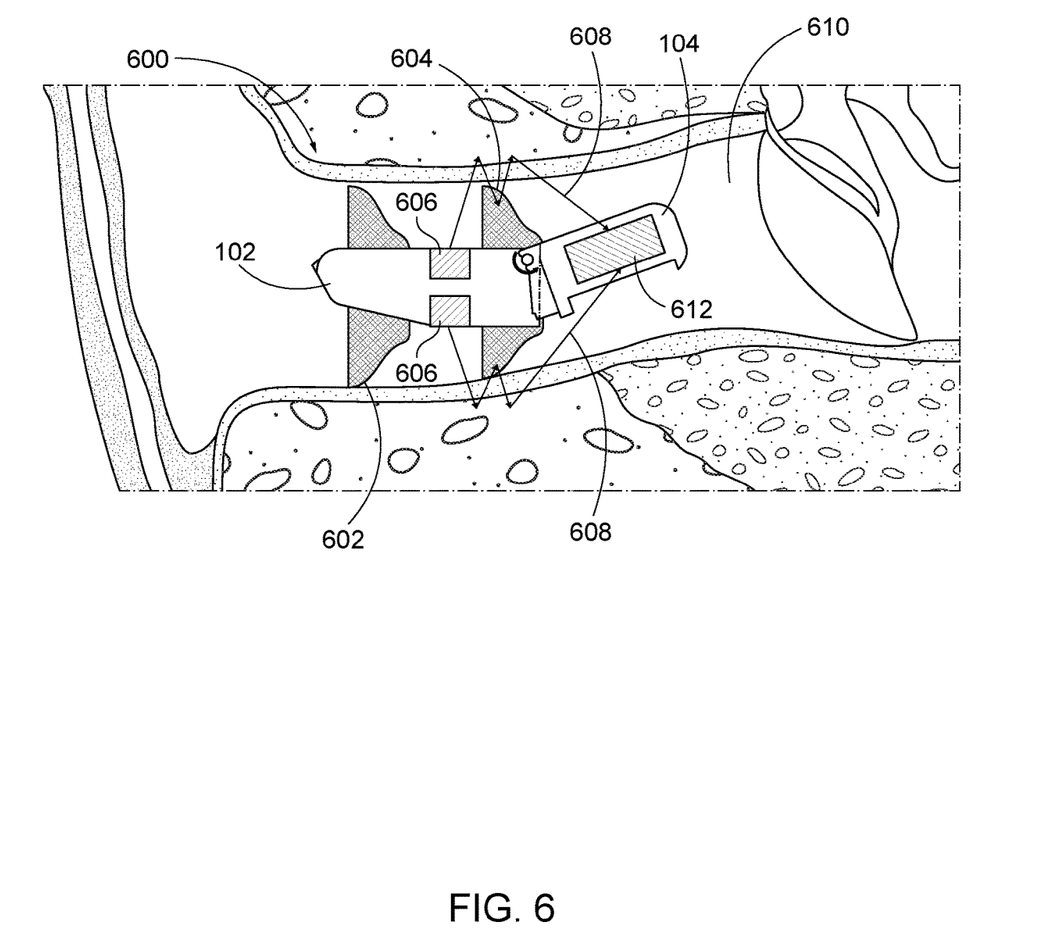
FIGS. 6-10 illustrate various example configurations of light sources and seals for in-ear devices according to the present disclosure.

The seal 400 also has an internal aperture 404 through which the lateral housing 102 can be fitted such that the seal 400 surrounds the lateral housing 102. An example in-ear device 500 having a lateral seal 502 around the lateral housing 102 and medial seal 504 around the medial articulating head 104 is illustrated in FIGS. 5A and 5B. As seen therein, preferably the seals 502, 504 are flared toward the lateral direction (thereby having a larger circumference at a lateral side than a medial side) to facilitate smooth insertion of the device 500 into the ear. The seal 400 is preferably an opaque casted silicone foam. However, in some embodiments a medially located seal (such as seal 504 in FIGS. 5A and 5B) may be transparent to allow light from the light source(s) of the device 100 to pass to the photodetector, or reflective to retransmit light through the walls of the ear canal, depending on its location relative to the photodetector.

FIGS. 6 to 10 illustrate various example configurations of light sources and seals of in-ear devices according to the present disclosure. According to a first example configuration illustrated in FIG. 6, an in-ear device 600 includes a lateral seal 602 at the lateral end of the lateral housing 102 and a medial seal 604 at the medial end of the lateral housing 102. LEDs 606 are housed in a middle portion of the lateral housing 102 between the seals 602, 604. The LEDs 606 are preferably angled to transmit light 608 into the walls of the ear canal 610 and toward the tympanic membrane, such that light 608 is transmitted through blood vessels of the ear canal and reflected by the blood vessels, cartilaginous tissue, bone, and/or other physiological structures back into the ear canal 610 where it can be detected by the photodetector 612. In such an embodiment, at least the medial seal 604 may be of a reflective material to re-transmit light that is reflected back into the ear canal 610 lateral to the photodetector 612 back into the walls of the ear canal 610 and further toward the photodetector 612.

Figure 7:
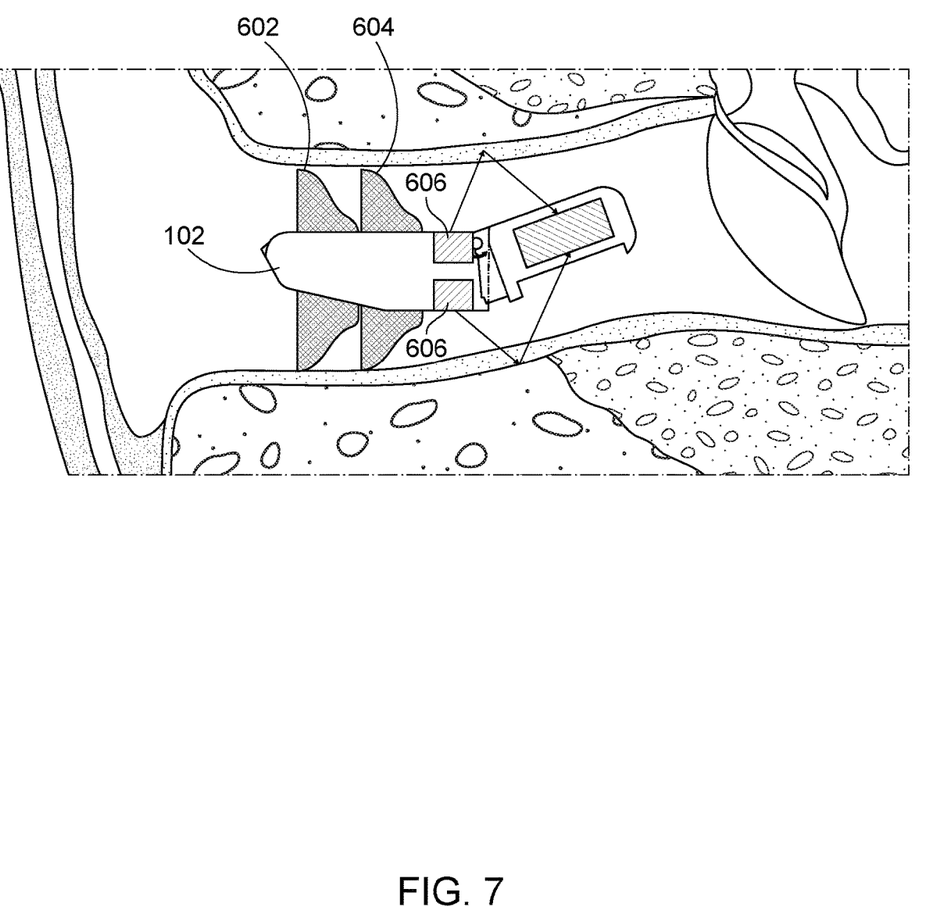
Figure 8:
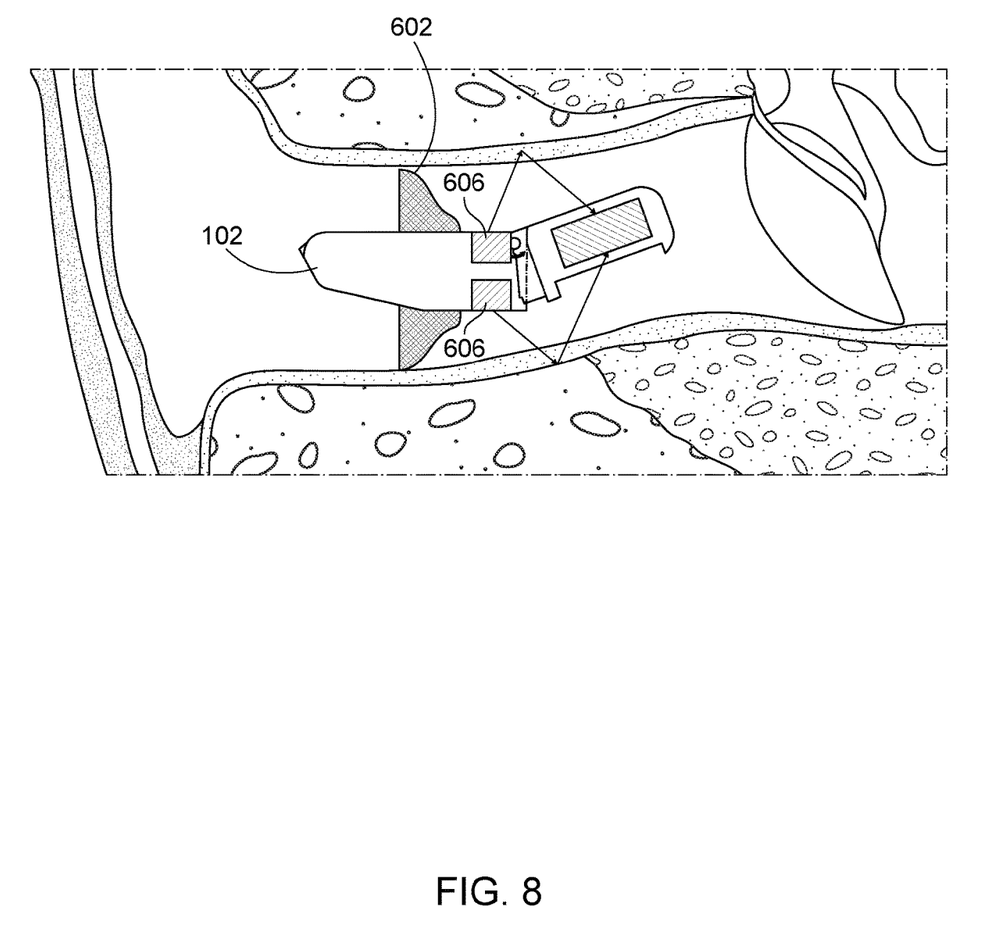
Figure 9:
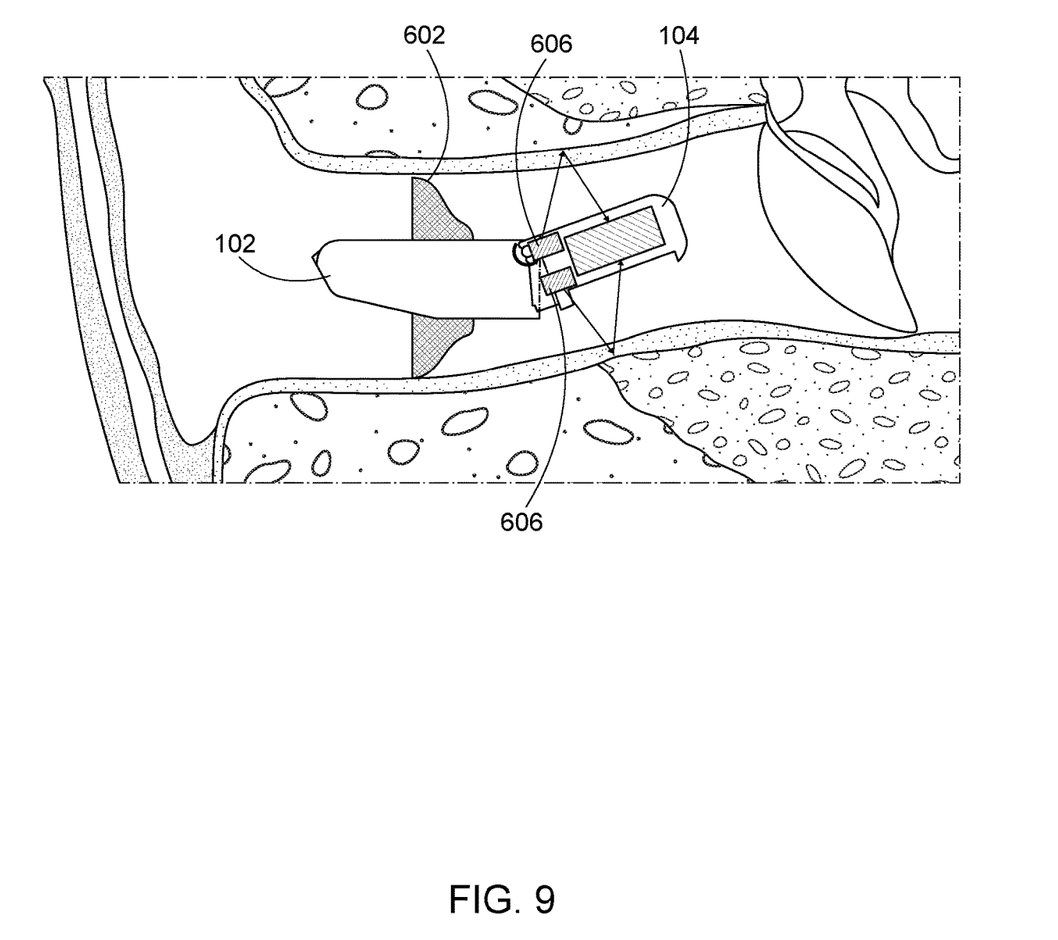

In another embodiment illustrated in FIG. 7, the LEDs 606 may be located at the medial end of the lateral housing 102. In such an embodiment, the lateral and medial seals 602, 604 are both located laterally to the LEDs 606. In a variation of this embodiment illustrated in FIG. 8, only a lateral seal 602 is provided laterally to the LEDs 606, at either a middle portion or a lateral portion of the lateral housing 102. In still another variation illustrated in FIG. 9, the LEDs 606 may be located in the medial articulating head 104, with one or more lateral seals 602 provided around any portion of the lateral housing 102. The embodiment illustrated in FIG. 9 shows one lateral seal 602 at a middle portion of the lateral housing 102.

Figure 10:
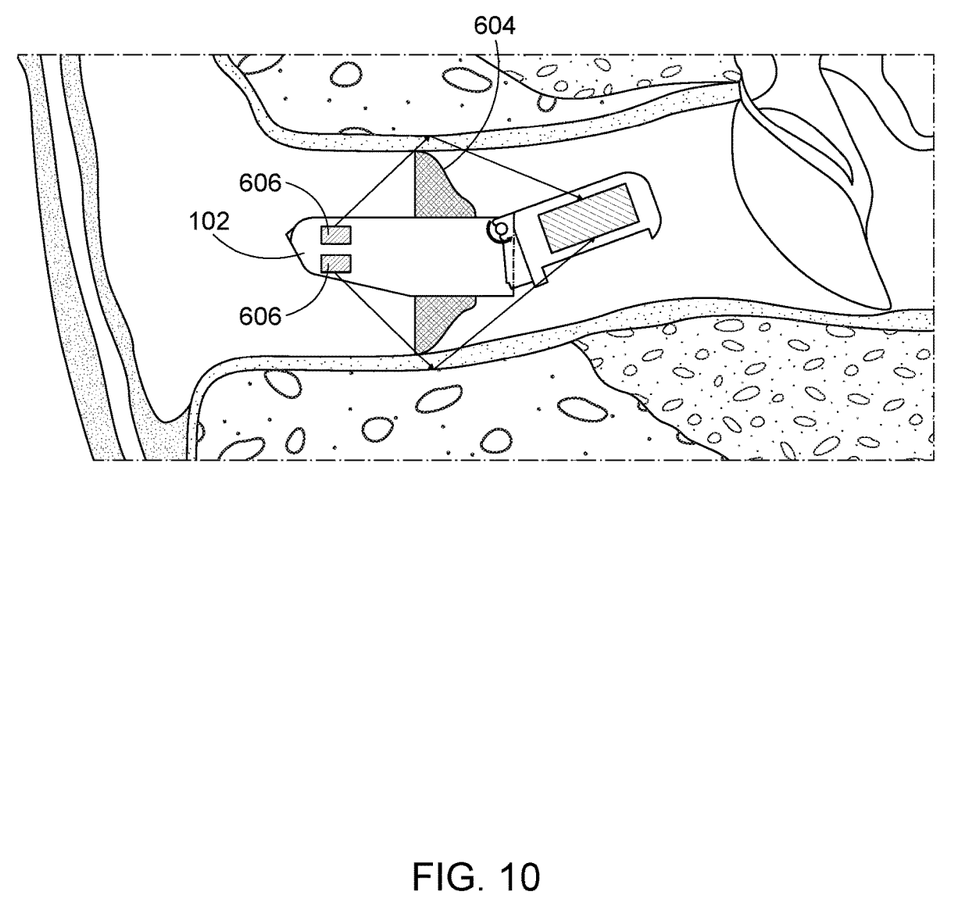

According to another embodiment illustrated in FIG. 10, the LEDs 606 are provided at a lateral end of the lateral housing 102 with one or more medial seals 604 located medially to the LEDs 606. As shown in FIG. 10, one medial seal 604 is provided at a middle portion of the lateral housing 102.

In any embodiment, a seal may be provided on the articulating head 104, for example as shown in FIGS. 5A and 5B, so long as the photodetector in the medial articulating head 104 is still exposed to light from the light source. In these embodiments, the seal may be transparent to light from the light source or be positioned more laterally or more medially than the photodetector so that the photodetector is not directly covered by the seal itself. By providing a seal on the articulating head 104, it is possible to further secure the device in tortuous ear canal shapes by providing an articulating seal.

What we claim is:

1. An optical sensor device comprising:
   an audio receiver configured to deliver a sound to a subject;
   a light source;
   a photodetector;
   a lateral body that houses the audio receiver;
   a medial head that houses the photodetector; and
   a seal surrounding a portion of the lateral body or the medial head,
   wherein the photodetector is located medial to the seal, and
   wherein the optical sensor device is configured to be inserted into an ear canal of the subject such that the medial head is closer than the lateral body to the tympanic membrane of the subject.

2. The optical sensor device of claim 1, wherein the audio receiver is communicatively coupled to a sound processor configured to provide an audio signal to the audio receiver, the audio signal representative of the delivered sound.

3. The optical sensor device of claim 2, wherein the sound processor is communicatively coupled to a microphone configured to detect sound, wherein the audio signal is representative of the detected sound.

4. The optical sensor device of claim 1, wherein an inner surface of the seal is corrugated such that the seal is configured to buckle upon application of radial pressure.

5. The optical sensor device of claim 1, wherein the medial head is an articulating head that is pivotably attached to the lateral body about an articulation joint.

6. The optical sensor device of claim 5, wherein the medial articulating head is pivotable to at least 20 degrees relative to the lateral body.

7. The optical sensor device of claim 1, wherein the light source is a light emitting diode.

8. The optical sensor device of claim 1 comprising two seals, wherein:
   a first seal of the two seals is located at a lateral end of the lateral body,
   a second seal of the two seals is located at a medial end of the lateral body, and
   the light source is located between the lateral end and the medial end of the lateral body.

9. The optical sensor device of claim 1 comprising two seals, wherein:
- a first seal of the two seals is located at a lateral end of the lateral body,
- the light source is located at a medial end of the lateral body, and
- a second seal of the two seals is located between the lateral end and the medial end of the lateral body.

10. The optical sensor device of claim 1, wherein the light source is housed in the lateral body and is located medial to the seal.

11. The optical sensor device of claim 1, wherein the light source is housed in the lateral body and is located lateral to the seal.

12. The optical sensor device of claim 1, wherein the light source is housed in the medial head and the seal is located at the lateral body.

13. The optical sensor device of claim 1, wherein when the optical sensor device is inserted into an ear canal of the subject, the optical sensor device is at least partially located in a bony region of the ear canal.

14. The optical sensor device of claim 1, wherein the optical sensor device is configured to perform photoplethysmography (PPG) based on light detected by the photodetector.

15. An optical sensor device comprising:
- an audio receiver communicatively coupled to a sound processor, the audio receiver being configured to deliver sound based on an audio signal provided by the sound processor to a subject;
- a light source configured to emit light into a wall of an ear canal of the subject;
- a photodetector configured to detect the emitted light that has been reflected and/or absorbed and reemitted by physiological structures within the wall of the ear canal;
- a lateral body that houses the audio receiver;
- a medial articulating head that houses the photodetector; and
- a corrugated seal configured to buckle upon application of radial pressure, the seal surrounding a portion of the lateral body, wherein:
- the medial head is pivotably attached to the lateral body about an articulation joint such that the medial head is pivotable to at least 20 degrees relative to the lateral body, and
- the optical sensor device is configured to be inserted into an ear canal of a subject such that the medial articulating head is closer than the lateral body to the tympanic membrane of the subject and the optical sensor device is at least partially located in a bony region of the ear canal.

* * * * *